United States Patent [19]

Kurtzman et al.

[11] 4,359,534

[45] Nov. 16, 1982

[54] **CONVERSION OF D-XYLOSE TO ETHANOL BY THE YEAST *PACHYSOLEN TANNOPHILUS***

[75] Inventors: Cletus P. Kurtzman, Peoria; Rodney J. Bothast, East Peoria; James E. VanCauwenberge, Normal, all of Ill.

[73] Assignee: The United States of America as represented by the Secretary of Agriculture, Washington, D.C.

[21] Appl. No.: 258,483

[22] Filed: Apr. 28, 1981

[51] Int. Cl.$^3$ .............................................. C12P 7/06
[52] U.S. Cl. ................................... 435/161; 435/163; 435/164; 435/165
[58] Field of Search ............... 435/161, 162, 163, 164, 435/165, 930

[56] References Cited

U.S. PATENT DOCUMENTS

2,481,263  9/1949  Tsuchiya et al. .............. 435/161 X

FOREIGN PATENT DOCUMENTS

884822  3/1960  United Kingdom ................ 435/930

OTHER PUBLICATIONS

S. L. Rosenberg, "Fermentation of Pentose Sugars to Ethanol and Other Neutral Products by Microorganisms," Enzyme Microbiol. Technol. 2: 185–193 (1980).

G. C. Avgerinos et al., "A Novel Single Step Microbial Conversion of Cellulosic Biomass to Ethanol," Presented at the International Fermentation Symposium, London, Ontario, Canada, Jul. 1980 (to be published in Proceedings).

P. Y. Wang et al., "Fermentation of D-Xylose by Yeasts Using Glucose Isomerase in the Medium to Convert D-Xylose to D-Xylulose," Biotechnol. Lett. 2(6): 279–284 (1980).

C. S. Gong et al., "Production of Ethanol from D-Xylose by Using D-Xylose Isomerase and Yeasts," Appl. Environ. Microbiol. 41(2): 430–436 (Feb. 1981).

*Primary Examiner*—Robert A. Yoncoskie
*Attorney, Agent, or Firm*—M. Howard Silverstein; David G. McConnell; Curtis P. Ribando

[57] ABSTRACT

A method is disclosed for converting D-xylose to ethanol relying on the unique ability of the yeast *Pachysolen tannophilus* to ferment this five-carbon sugar without the use of added enzymes. This process will be particularly useful in the production of ethanolic fuel from plant biomass.

11 Claims, No Drawings

CONVERSION OF D-XYLOSE TO ETHANOL BY THE YEAST *PACHYSOLEN TANNOPHILUS*

BACKGROUND OF THE INVENTION

1. Field of the Invention

This invention relates to a fermentation process useful in the production of ethanol from renewable plant biomass. An ever-increasing interest in the development of such processes has stemmed from the current emphasis on utilizing ethanol as an alternative liquid fuel.

Plant solids contain three major components: lignin, cellulose, and hemicellulose. The lignin is a polyphenolic macromolecule which binds together the cellulose and adds rigidity to the plant material. It is not convertible to alcohol. The cellulose is a homopolymer of glucose, and upon separation from the lignin yields a hydrolyzable source of fermentable hexose sugar. Hemicellulose comprises up to about 35% of the plant solids and is readily hydrolyzed with dilute acid under mild conditions to a mixture of sugars, with D-xylose (a pentose) as the major product. However, the lack of an effective fermentation process to use D-xylose has seriously diminished the practicality of plant biomass as a source of petroleum-sparing compounds.

2. Description of the Prior Art

Bacteria and fungi have previously been recognized for their ability to convert pentoses to ethanol or at least have a participating role in the conversion pathway. A review S. L. Rosenberg ["Fermentation of Pentose Sugars to Ethanol and Other Neutral Products by Microorganisms," Enzyme Microbiol. Technol. 2: 185-193 (1980)] teaches, for example, that *Fusarium oxysporium* in resting cell suspension will ferment D-xylose to approximately equimolar amount of ethanol, $CO_2$, and acetic acid. In growing cultures, the proportion of ethanol and $CO_2$ to acetate is somewhat increased. Certain bacterial species of Escherichia, Spirochaeta, Aeromonas, bacillus, and Aerobacter are also shown to produce ethanol from pentose sugars, but in relatively low yield and usually in conjunction with 2,3-butanediol and a variety of organic acids. G. C. Avgerinos et al. ["A Novel Single Step Microbial Conversion of Cellulosic Biomass to Ethanol," presented at the International Frementation Symposium, London, Ontario, Canada, July 1980] reports an attempt to convert corn stover directly to ethanol by means of a mixed culture of mutant strains of *Clostridium thermocellum* and *C. thermosaccharolyticum*. While the latter strain proved effective in utilizing the pentosans produced by the *C. thermocellum*, the overall alcohol yield was only 50% of the theoretical maximum.

It has long been recognized that yeasts have the ability to stoichiometrically convert 1 mole of glucose to 2 moles each of ethanol and $CO_2$. Also, yeasts are able to assimilate natural pentoses oxidatively, but they are not able to ferment them to ethanol as they can glucose (Rosenberg, supra, paragraph bridging pages 187 and 188). Several yeasts have recently been shown to have the capacity for fermenting D-xylulose, a keptopentose. In connection therewith, Wang et al. [Biotechnol. Lett. 2(6): 279-284 (1980)] demonstrated the feasibility of adding glucose isomerase to a D-xylose-containing medium, thereby converting the substrate in situ to the fermentable xylulose form. However, the ultimate rate of ethanol production was low and the yield was a mere 10% of the theoretical. Gong et al. [Appl. Environ. Microbiol. 41(2): 430-436 [February 1981)] reportedly bolstered the yield by this technique to greater than 80%, but on a commercial scale the enzyme-assisted conversion will most likely remain economically unattractive.

SUMMARY OF THE INVENTION

We have now surprisingly discovered a species of yeast which will ferment D-xylose without added enzymes, thereby having utility in a process for converting plant biomass to ethanol. The yeast is *Pachysolen tannophilus*, and is remarkably adapted for fermenting the xylose-containing substances derived from the hydrolysis of lignocellulosic plant materials.

In accordance with this discovery, it is an object of the invention to provide a novel method for directly fermenting the D-xylose in xylose-containing substances to ethanol.

It is also an object of the invention to provide an efficient and economical process useful in the product of an alternative liquid fuel from plant biomass material.

Another object of the invention is to provide a method for conducting a xylose fermentation under conditions inhibitory to competing organisms and side reactions.

Other objects and advantages of this invention will become readily apparent from the ensuing description.

DETAILED DESCRIPTION OF THE INVENTION

The yeast *Pachysolen tannophilus* for use herein is sometimes referred to by the synonomous names *Pa. pelliculatus* and *Hansenula tannophilus*. The type strain CBS 4044 (NRRL Y-2460) was originally isolated from concentrated tanning liquors and was designated by Boidin and Adzet in 1957. A complete taxonomic description is as follows:

Growth on malt extract agar: After 3 days at 25° C., the cells are spheroidal to ellipsoidal $(1.5-5.0)\times(2.0-7.0)$ µm. and usually have one or two buds. Growth is mucoid to butyrous and tannish-white.

Dalmau plate culture on morphology agar: After 7 days at 25° C., growth under the coverglass exhibits simple undifferentiated pseudohyphae as well as occasional highly branched strands. Aerobic growth is tannish-white, glistening, mucoid, low convex with margin entire and with a faint smell of esters.

Formation of ascospores: The ascus forms when a vegetative cell produces a stout tube, generally at one end. Depending upon the culture medium, and perhaps other factors, tubes may be quite short or up to 60 µm. in length and are straight or curved. The tip of the tube enlarges to form the ascus, and consequently, the tube may be regarded as an ascophore. Asci contain up to four hemispheroidal ascospores that have a narrow ledge at the base. The ascus wall dehisces releasing the spores. Once this happens, it is seen that the ascus formed within a V-shaped notch at the end of the ascophore. Ascophore walls appear greatly thickened and become quite refractile. This characteristic of highly refractile ascophores bearing terminal asci makes Pachysolen readily identifiable under the light microscope even at moderate magnifications.

Asci may be conjugated or unconjugated depending upon the strain examined. The type strain NRRL Y-2460 forms unconjugated asci while NRRL Y-2461, Y-2462, and Y-2463 have conjugated asci. All cultures sporulated on YM agar at 25° C. after about 1 week.

Single spore isolates from NRRL Y-2460 gave sporogenous colonies; therefore, the species appears homothallic (Wickerham, 1970).

Spores were observed on YM, Gorodkowa, and malt extract agar media.

| Fermentation: | | | |
|---|---|---|---|
| Glucose | + | Maltose | − |
| Galactose | − | Lactose | − |
| Sucrose | − | Raffinose | − |
| Assimilation of carbon compounds: | | | |
| Galactose | + | Raffinose | − | Erythritol | + |
| Sucrose | − | Soluble starch | − | Ribitol | + |
| Maltose | − | D-Xylose | + | D-Mannitol | + |
| Cellobiose | + or s | L-Arabinose | + | Succinic acid | + |
| Trehalose | − | D-Ribose | − or s | Citric acid | − |
| Lactose | − | L-Rhamnose | − | Inositol | − |

Assimilation of nitrate: +

Growth in vitamin-free medium: −

Growth in 10% sodium chloride plus 5% glucose in yeast nitrogen base: +

Growth at 37° C.: +

G+C: 43.0 mol. %, one strain (Nakase and Komagata, 1968)

In addition to the above-mentioned fermentable substrate, we have unexpectedly found that *Pa. tannophilus* has the unique ability among yeasts to also ferment D-xylose. All known strains thereof including NRRL Y-2460, Y-2461, Y-2462, Y-2463, and Y-6704 share this characteristic and are therefore contemplated for use in the disclosed process, without limitation thereto.

The substrates which are suitable for ethanol production by the instant method include all xylose-containing substances provided that the other constituents therein do not grossly interfere with the fermentative pathway. Of particular interest of course are lignocellulosic degradation products especially the hydrolysate of hemicellulose, or of hemicellulose-containing feedstocks such as wood, grasses, and agricultural crop residues as well known in the art. It is understood that the naturally occurring form of pentose sugar in these materials is predominantly D-xylose, which is the entity directly acted upon by the yeast. Available glucose will also be fermented.

The fermentation is conducted in an aqueous medium under conditions sufficient to maintain cell viability and to promote the xylose to ethanol conversion. While it will proceed under non-growth conditions, the overall alcohol production is generally enhanced if the organisms are allowed to propagate. The medium should therefore contain a suitable source of nitrogen. Mineral supplements and other nutrients may also be added as readily deemed necessary by a person in the art. For purposes of practicality in relation to recovery, the total fermentable sugar concentration should be maintained at a level sufficient to yield at least about 15 g./l. ethanol in the final broth. The upper limit of fermentable sugar concentration is that which causes substantial retardation of the specific ethanol production rate; that is, the rate of ethanol production per unit of yeast cells. For the strains mentioned above, xylose levels meeting these criteria would be within the range of approximately 50 g./l. to approximately 250 g./l., with a range of 50-150 g./l. being preferred. When the ethanol concentration exceeds about 19 g./l. in the medium, it too begins to inhibit the specific production rate.

While oxygen is not essential to fermentation, cell growth and the concomitant ethanol production are greatly enhanced when the medium is oxygenated by aeration. Under conditions of rapid growth, the calculated oxygen demand per gram of cell mass is approximately 9.2 mmoles $O_2$/hr.

Cell growth rate, cell concentration, and ethanol output are all favored by a low pH environment. The operable range for conducting the fermentation is from about 2 to 7. However, the ethanol yield at pH's in the range of 2.5–5.5 is more than twice that obtained at pH's over 5.5, indicating that at higher pH's, the xylose enters a metabolic pathway other than that leading to ethanol formation. The best results occur at a pH approximating 2.5. This phenomenon is somewhat unexpected in light of previous reports that pentose consumption in yeasts is generally most efficient under alkaline conditions rather than acidic conditions. Since the cellular functions of most organisms are inhibited when the pH is so low *Pa. tannophilus* is able to favorably compete against undesirable culture contaminants. It is, therefore, not necessarily essential to sterilize the substrate and other constituents of the culture medium.

Cultivation temperatures in the range of about 28°–35° C. are preferred, with 32° C. being about optimal for cell growth rate, specific ethanol production rate, and overall ethanol yield. The fermentation will in fact proceed at temperatures of 15° C. or below, though the rates and yield are expectedly lower.

In a typical batch-type fermentation, an acidified growth medium containing the desired concentration of xylose-containing substance is inoculated with precultured *Pa. tannophilus* to provide an initial yeast density of about 0.01 g./l. The pH and temperature are controlled at predetermined values within the ranges defined above, and the culture is continuously aerated and stirred throughout the incubation period. Depending upon the initial concentration and the conditions of incubation, the xylose substrate is usually depleted in about 3 to 10 days, after which the fermentation is halted. The ethanol-enriched medium is then recovered and may be processed by distillation or other means as known in the art for isolating the ethanol or desired ethanolic fraction.

The proportion of xylose assimilated by *Pa. tannophilus* during cell growth is small (about 10%) compared to that which is fermented. Though the actual fermentative pathway is not known, it is apparent from the following equation that the theoretical ethanol yield could be as high as 0.51 g./g. of xylose consumed:

$$C_5H_{10}O_5 \rightarrow \tfrac{5}{3} C_2H_5OH + \tfrac{5}{3} CO_2$$

(D-xylose)  (ethanol)

Under the conditions specified herein, yields as high as 0.34 g./g. have been obtained.

The following examples are intended only to further illustrate the invention and are not intended to limit the scope of the invention defined by the claims.

EXAMPLE 1

Preparation of Media and Precultures

The following stock solutions were initially prepared:

|  | g./l. |
|---|---|
| Solution A - Trace minerals | |

| | g./l. |
|---|---|
| CaO | 1.10 |
| ZnO | 0.40 |
| FeCl$_3$.6H$_2$O | 5.40 |
| MgO | 0.36 |
| CuSO$_4$.5H$_2$O | 0.25 |
| CoCl$_2$.6H$_2$O | 0.24 |
| H$_3$BO$_3$ | 0.06 |
| HCl (concentrated) | 13.0 ml./l. |
| Solution B | |
| MgO | 10.1 g./l. |
| HCl (concentrated) | 45.0 ml./l. |
| Solution C | |
| urea | 64.0 |
| KH$_2$PO$_4$ | 12.0 |
| Na$_2$HPO$_4$ | 1.8 |

One liter of culture medium was prepared by first combining 10 ml. solution A, 10 ml. solution B, 100 ml. solution C, and 10 g. yeast extract to form a 120-ml. volume. After centrifuging to remove any precipitates, the mixture was autoclaved. The pH of the cooled, sterile solution was then adjusted to 4.5 with about 1 ml. of 2 N HCl in order to redissolve any precipitates formed during sterilization. D-Xylose (50 g.) was dissolved in enough distilled water to form an 880-ml. volume which was then autoclaved and combined with the mineral solution.

A lyophilized culture of *Pa. tannophilus*, strain NRRL Y-2460, was obtained from the Agricultural Research Culture Collection (NRRL) in Peoria, IL. Stock cultures prepared from the lyophilizate were maintained on agar slants at 32° C. The slant medium contained 3.0 g./l. yeast extract, 3.0 g./l. malt extract, 5.0 g./l. peptone, 10.0 g./l. dextrose, and 20.0 g./l. agar.

Inocula were prepared by transferring organisms by loop from the stock cultures to 48-hr. slants and then to 125-ml. Erlenmeyer flasks containing 50 ml. of the xylose-containing culture medium (50 g./l. xylose, initial pH=4.5). These precultures were shaken at 28° C. and 150 r.p.m. for 48 hr. prior to use.

EXAMPLES 2-7

Four hundred-milliliter samples of the culture medium (50 g./l. xylose, initial pH=4.5) prepared in Example 1 and placed in 500 ml. Erlenmeyer flasks were inoculated with a sufficient quantity of the yeast preculture to give an initial yeast density of 0.01 g./l. The flasks were closed with gauze-covered cotton stoppers to permit efficient oxygen transfer and were shaken at 200 r.p.m. for approximately 160 hr. in a "New Brunswick Aquatherm" water bath shaker. Samples of less than 4 ml. were periodically drawn from analysis. The maximum rates of cell growth, xylose consumption, and ethanol production per unit of cells as well as the overall ethanol yield were determined as a function of temperature. The results are reported in Table I below.

EXAMPLE 8

In order to verify that the resultant ethanol was the product of xylose conversion, the procedure of Example 4 conducted at 25° C. was repeated except that xylose was omitted from the medium. The xylose-free medium did not give rise to any ethanol production, and it allowed the yeast population to grow to a final density of merely 4% of that attained in Example 4 when xylose was present in an initial concentration of 50 g./l.

EXAMPLES 9-13

Effect of Initial Xylose Concentration

The procedure of Examples 2-7 was repeated except that the temperature was held constant at 25° C. (as in Example 4) and the initial xylose concentration was varied. The initial rate of cell growth, the maximum rates of xylose consumption and ethanol production per unit of cells, and the overall ethanol yield were determined as a function of the initial xylose concentration. The results are reported in Table II below.

EXAMPLES 14-17

Effect of pH

The procedure of Examples 2-7 was repeated with the temperature held at 25° C. as in Example 4 except that the fermentations were conducted in batch fermenters with 10 l. of the culture medium, and the pH was controlled within ±0.05 pH units at various predetermined values by the automated addition of 1 N NaOH. The aeration rate was controlled at 0.75 l./min. and the stirring rate at 200 r.p.m. for Examples 14 and 15 and 100 r.p.m. for Examples 16 and 17. The fermentations of Examples 14 and 15 were terminated after 146 hr. and those of Examples 16 and 17 after 138 hr. The maximum rates of cell growth, xylose consumption, and ethanol production per unit of cells as well as the overall ethanol yield were determined as a function of pH. The results are reported in Table III below.

TABLE I

Effect of Temperature

| Example | Temp. (°C.) | Max. cell growth rate (hr.$^{-1}$) | Max. xylose consumption rate (g./g. · hr.) | Max. EtOH production rate (g./g. · hr.) | EtOH yield (g./g.)$^a$ |
|---|---|---|---|---|---|
| 2 | 15 | 0.09 | 0.12 | 0.05 | 0.26 |
| 3 | 20 | 0.14 | 0.26 | 0.06 | 0.27 |
| 4 | 25 | 0.16 | 0.32 | 0.07 | 0.27 |
| 5 | 28 | 0.19 | 0.44 | 0.11 | 0.28 |
| 6 | 32 | 0.24 | 0.49 | 0.12 | 0.34 |
| 7 | 40 | 0.06 | 0 | 0 | 0 |

$^a$Ethanol yield = $\dfrac{\text{grams EtOH}_{final} - \text{grams EtOH}_{initial}}{\text{grams xylose}_{initial} - \text{grams xylose}_{final}}$

TABLE II

Effect of Initial Xylose Concentration

| Example | Initial xylose conc. (g./l.) | Initial cell growth rate (hr.$^{-1}$) | Max. xylose consumption rate (g./g. · hr.) | Max. EtOH production rate (g./g. · hr.) | EtOH yield (g./g.)$^a$ |
|---|---|---|---|---|---|
| 9 | 55 | 0.22 | 0.3 | 0.09 | 0.29 |
| 10 | 115 | 0.19 | 0.4 | 0.09 | 0.24 |
| 11 | 158 | 0.13 | 0.4 | 0.08 | 0.21 |
| 12 | 210 | 0.09 | 0.4 | 0.06 | ...$^b$ |
| 13 | 255 | 0.07 | 0.4 | 0.05 | ...$^b$ |

$^a$Ethanol yield = $\dfrac{\text{grams EtOH}_{final} - \text{grams EtOH}_{initial}}{\text{grams xylose}_{initial} - \text{grams xylose}_{final}}$
$^b$Fermentation not carried to completion.

EXAMPLES 18-22

Having determined that *Pa. tannophilus* NRRL Y-2460 will ferment xylose to ethanol, the remaining strains on deposit in the Agricultural Research Culture Collection were also tested for this characteristic by means of a standard survey procedure. Each was tested on a control medium (no carbon source), a glucose medium, and a xylose medium. A stock basal medium was prepared from 4.5 g. powdered yeast extract, 7.5 g. peptone, 1000 ml. distilled water, and enough bromthymol blue to give a sufficiently dense green color. Two-milliliter quantities of the medium were placed in 150×12 mm. Durham tubes fitted with inserts measuring 50×6 mm., followed by the addition of distilled water for the controls, or 1 ml. of a sterilized 6% aqueous solution of either glucose or xylose. The fermentation media were then inoculated with 0.1 ml. of a cell suspension made by suspending the growth of a 48-hr. malt extractyeast extract agar slant in 4.5 ml. sterile distilled water. The cultures were incubated at 28° C. for 61 days. Periodically, the tubes were shaken and visually observed for the amount of gas in the inserts as an indicator of the degree of fermentation. Based upon prior study with strain Y-2460, the gas was assumed to be $CO_2$. The results are reported in Table IV below. All controls throughout the study gave negative readings for gas.

EXAMPLE 23

A culture medium was prepared comprising the following components:

| | |
|---|---|
| water | 9 l. |
| xylose | 500 g. |
| salt-amino acid mix: | |
| $(NH_4)_2SO_4$ | 50 g. |
| $KH_2PO_4$ | 10 g. |
| $MgSO_4$ | 5 g. |
| NaCl | 1 g. |
| $CaCl_2$ | 1 g. |
| methionine | 0.2 g. |
| tryptophane | 0.2 g. |
| histidine | 0.1 g. |
| vitamin-mineral mix: | 10 ml. |

| Vitamins | g./l. |
|---|---|
| biotin | 0.002 |
| Ca panthotheniate | 0.400 |
| folic acid | 0.002 |
| inositol | 2.000 |
| niacin | 0.400 |
| p-aminobenzoic acid | 0.200 |
| pyridoxine.HCl | 0.400 |
| riboflavin | 0.200 |
| thiamine.HCl | 0.400 |

| Minerals | g./l. |
|---|---|
| $B(OH)_3$ | 0.500 |
| $CuSO_4$ | 0.040 |
| KI | 0.100 |
| $FeCl_3$ | 0.200 |
| $MnSO_4$ | 0.400 |
| $Na_2MoO_4.H_2O$ | 0.200 |
| $ZnSO_4$ | 0.400 |

The water, xylose, and salt-amino acid mix were combined and sterilized. After the mixture cooled to room temperature, the vitamin-mineral mix was added, and the medium was placed in a 10-l. fermenter. The medium was then inoculated with Pa. tannophilus Y-2460 by the addition of 1 l. of a 48-hr. yeast-malt preculture comprising 3 g./l. yeast extract, 3 g./l. malt extract, 10 g./l. dextrose, and 5 g./l. peptone. The culture was incubated at 28° C. for 14 da. and checked regularly for xylose, ethanol, and pH. The results are reported in Table V below. The decline in ethanol content after day 6 is attributed to evaporation from the medium and perhaps assimilation by the yeast cells.

EXAMPLES 24-33

The effectiveness of Pa. tannophilus on a mixed medium and its compatibility in mixed culture was ascertained by the following set of experiments. A series of three culture media were prepared in accordance with Example 1, except that the carbon source was varied. One medium contained 50 g./l. D-xylose, another contained 50 g./l. dextrose, and the third contained a mixture of 50 g./l. D-xylose and 50 g./l. dextrose. Three flasks were prepared with each of the single-sugar media, and four with the mixed medium. These flasks were inoculated with either Pa. tannophilus NRRL Y-2460 or Saccharomyces uvarum NRRL Y-1346, or a mixture thereof by loop from slants incubated at 32° C. for 2 da. and then left at room temperature until used. The inoculated flasks were shaken at 100 r.p.m. at a constant temperature of 28° C. for 4 da., after which the ethanol content was determined. The results are set forth in Table VI below.

It is understood that the foregoing detailed description is given merely by way of illustration and that modification and variations may be made therein without departing from the spirit and scope of the invention.

TABLE III

| | | Effect of pH | | |
|---|---|---|---|---|
| Example | pH | Max. cell growth rate $(hr.^{-1})$ | Max. xylose consumption rate $(g./g. \cdot hr.)$ | Max. EtOH production rate $(g./g. \cdot hr)$ | EtOH yield $(g./g.)^a$ |
| 14 | 2.5 | 0.18 | 0.43 | 0.13 | 0.20 |
| 15 | 4.5 | 0.20 | 0.32 | 0.07 | 0.22 |
| 16 | 6.5 | 0.09 | 0.39 | 0.03 | 0.08 |
| 17 | 7.5 | 0.09 | 0 | 0 | ... |

$^a$Ethanol yield $= \dfrac{\text{grams EtOH}_{final} - \text{grams EtOH}_{initial}}{\text{grams xylose}_{initial} - \text{grams xylose}_{final}}$

TABLE IV

| Example | Strain | Carbon[a] source | Percent gas Days after inoculation | | | | | | | | | | | |
|---|---|---|---|---|---|---|---|---|---|---|---|---|---|---|
| | | | 1 | 2 | 4 | 7 | 10 | 12 | 14 | 17 | 22 | 28 | 36 | 61 |
| 18A | Y-2460 | glucose | 0 | 15 | 100 | 90 | 60 | 15 | 15 | 10 | 5 | 5 | 5 | 5 |
| B | | xylose | 0 | 0 | 0 | 0 | 1 | 60 | 95 | 85 | 60 | 15 | 5 | 0 |
| 19A | Y-2461 | glucose | 0 | 2 | 60 | 100 | 80 | 25 | 15 | 10 | 5 | 5 | 5 | 5 |
| B | | xylose | 0 | 0 | 0 | 0 | 0 | 3 | 10 | 45 | 30 | 10 | 5 | 5 |
| 20A | Y-2462 | glucose | 0 | tr | 5 | 90 | 80 | 15 | 10 | 5 | 5 | 5 | 5 | 5 |
| B | | xylose | 0 | 0 | 0 | tr | 5 | 85 | 100 | 95 | 80 | 60 | 15 | 5 |
| 21A | Y-2463 | glucose | 0 | 5 | 90 | 90 | 80 | 30 | 15 | 15 | 5 | 5 | 5 | 5 |
| B | | xylose | 0 | 0 | 0 | tr | 15 | 70 | 100 | 80 | 40 | 10 | 5 | 0 |
| 22A | Y-6704 | glucose | 0 | 3 | 80 | 100 | 75 | 25 | 15 | 15 | 5 | 5 | 5 | 5 |
| B | | xylose | 0 | 0 | 0 | 0 | 3 | 65 | 95 | 90 | 40 | 15 | 5 | 5 |

[a]All basal medium controls without sugar gave negative readings for gas.

TABLE V

| Day | Xylose (g./l.) | Ethanol (% w/w) | pH |
|---|---|---|---|
| 0 | 45 | 0.05 | 4.15 |
| 1 | 39 | 0.20 | |
| 2 | 25 | 0.50 | |
| 3 | 13 | 1.20 | |
| 4 | 6 | 1.60 | 2.70 |
| 5 | 0.6 | 1.10 | |
| 6 | 0 | 1.10 | 2.60 |
| 7 | 0 | 0.8 | 2.60 |
| 8 | 0 | 0.9 | 2.50 |
| 11 | 0 | 0.7 | |
| 12 | 0 | 0.5 | |
| 13 | 0 | 0.4 | 2.40 |
| 14 | 0 | 0.3 | |

TABLE VI

| | Initial substrate | | Inoculum | | Ethanol |
|---|---|---|---|---|---|
| Example | 50 g./l. xylose | 50 g./l. dextrose | Y-2460 | Y-1347 | (% w/w) |
| 24 | + | − | + | − | 1.0 |
| 25 | + | − | − | + | tr |
| 26 | + | − | + | + | 1.0 |
| 27 | − | + | + | − | 1.5 |
| 28 | − | + | − | + | 1.5 |
| 29 | − | + | + | + | 1.5 |
| 30 | + | + | + | − | 2.0 |
| 31 | + | + | − | + | 1.4 |
| 32 | + | + | + | + | 1.8 |
| 33 | + | + | + | + | 1.8 |

We claim:

1. A method for producing ethanol from a xylose-containing substance comprising the following steps:
   a. inoculating a medium containing said substance with the yeast *Pachysolen tannophilus;*
   b. fermenting said substance in said inoculated medium under conditions favorable for cell viability and for conversion of xylose to ethanol by the yeast, thereby enriching said medium with ethanol; and
   c. recovering said ethanol-enriched medium from the fermentation of step (b).

2. A method as described in claim 1 wherein the yeast *Pachysolen tannophilus* is a strain selected from the group consisting of NRRL Y-2460, NRRL Y-2461, NRRL Y-2462, NRRL Y-2463, and NRRL Y-6704.

3. A method as described in claim 1 wherein said xylose-containing substance is a lignocellulosic degradation product.

4. A method as described in claim 1 wherein said xylose-containing substance is a hemicellulose hydrolysate.

5. A method as described in claim 1 wherein the medium of step (a) also contains glucose and wherein the fermentation conditions of step (b) are also favorable for fermenting said glucose to ethanol.

6. A method as described in claim 1 wherein the fermentation conditions of step (b) are also favorable for cell growth.

7. A method as described in claim 6 wherein the medium is oxygenated, the pH is controlled within the range of about 2 to about 7, and the temperature is maintained within the range of about 10° to about 35° C.

8. A method as described in claim 6 wherein the pH is controlled at about 2.5 and the temperature is maintained at approximately 32° C.

9. A method as described in claim 1 wherein prior to the inoculation in step (a), said xylose is present in said medium at a concentration of less than about 150 g./l.

10. A method as described in claim 9 wherein said concentration is about 50 g./l.

11. A method as described in claim 1 and further comprising the step of isolating aqueous ethanol from the recovered ethanol-enriched medium.

* * * * *